United States Patent
Stone et al.

(10) Patent No.: US 7,749,250 B2
(45) Date of Patent: Jul. 6, 2010

(54) SOFT TISSUE REPAIR ASSEMBLY AND ASSOCIATED METHOD

(75) Inventors: Kevin T. Stone, Winona Lake, IN (US); Troy M. Walters, Plymouth, IN (US); Andrew Holst, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 506 days.

(21) Appl. No.: 11/347,661

(22) Filed: Feb. 3, 2006

(65) Prior Publication Data

US 2007/0185532 A1 Aug. 9, 2007

(51) Int. Cl.
*A61B 17/04* (2006.01)

(52) U.S. Cl. ...................................... 606/232

(58) Field of Classification Search ............. 606/74, 606/213, 215, 216, 232, 233; 24/129 D; 289/2, 17; 285/235; 623/13.15, 13.11
See application file for complete search history.

(56) References Cited

U.S. PATENT DOCUMENTS

| | | | |
|---|---|---|---|
| 26,501 | A | 12/1859 | Kendrick et al. |
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 401,677 | A | 4/1889 | Roeder |
| 417,805 | A | 12/1889 | Beaman |
| 487,304 | A | 12/1892 | Todd |
| 762,710 | A | 6/1904 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |

(Continued)

FOREIGN PATENT DOCUMENTS

AU 49572/64 3/1966

(Continued)

OTHER PUBLICATIONS

A. Weiler, et al; Biodegradierbare Interferenzschrauben in der Kreuzbandchirurgie; OP-Journal 14 pp. 278-284; 1998.

(Continued)

*Primary Examiner*—(Jackie) Tan-Uyen T Ho
*Assistant Examiner*—Dianne Dornbusch
(74) *Attorney, Agent, or Firm*—Harness Dickey

(57) ABSTRACT

A soft tissue repair assembly. The assembly includes a flexible member having first and second ends, and a strand passing through the flexible member. The strand has first and second strand ends extending through the flexible member, such that pulling at least one of the first and second strand ends changes the flexible member from a first shape suitable for insertion through soft tissue to a second shape suitable for securely lodging the soft tissue repair assembly relative to soft tissue.

17 Claims, 11 Drawing Sheets

U.S. PATENT DOCUMENTS

| | | |
|---|---|---|
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens |
| 3,590,616 A | 7/1971 | Schussler et al. |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |

| Patent | Date | Name |
|---|---|---|
| 4,312,337 A | 1/1982 | Donohue |
| 4,316,469 A | 2/1982 | Kapitanov |
| 4,326,531 A | 4/1982 | Shimonaka |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,705,040 A | 11/1987 | Mueller et al. |
| 4,708,132 A | 11/1987 | Silvestrini |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson et al. |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,848 A | 8/1988 | Hasson |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee |
| 4,784,126 A | 11/1988 | Hourahane et al. |
| 4,787,882 A | 11/1988 | Clarén |
| 4,790,297 A | 12/1988 | Luque |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,841,960 A | 6/1989 | Garner |
| 4,851,005 A | 7/1989 | Hunt et al. |
| 4,858,608 A | 8/1989 | McQuilkin |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Törmälä et al. |
| 4,969,886 A | 11/1990 | Cziffer et al. |
| 4,976,736 A | 12/1990 | White et al. |
| 4,978,350 A | 12/1990 | Wagenknecht |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,062,344 A | 11/1991 | Gerker |
| 5,062,843 A | 11/1991 | Mahony, III |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |

| | | | | | | |
|---|---|---|---|---|---|---|
| 5,116,337 A | 5/1992 | Johnson | | 5,360,431 A | 11/1994 | Puno et al. |
| 5,116,373 A | 5/1992 | Jakob et al. | | 5,362,294 A | 11/1994 | Seitzinger |
| 5,116,375 A | 5/1992 | Hofmann | | 5,364,400 A | 11/1994 | Rego, Jr. et al. |
| 5,123,913 A | 6/1992 | Wilk et al. | | 5,368,599 A | 11/1994 | Hirsch et al. |
| 5,127,785 A | 7/1992 | Faucher et al. | | 5,370,661 A | 12/1994 | Branch |
| 5,129,901 A | 7/1992 | Decoste | | 5,370,662 A | 12/1994 | Stone et al. |
| 5,129,902 A | 7/1992 | Goble et al. | | 5,372,146 A | 12/1994 | Branch |
| 5,129,904 A | 7/1992 | Illi | | 5,372,604 A | 12/1994 | Trott |
| 5,129,906 A | 7/1992 | Ross et al. | | 5,372,821 A | 12/1994 | Badylak et al. |
| 5,139,499 A | 8/1992 | Small et al. | | 5,374,268 A | 12/1994 | Sander |
| 5,139,520 A | 8/1992 | Rosenberg | | 5,379,492 A | 1/1995 | Glesser |
| 5,143,498 A | 9/1992 | Whitman | | 5,383,878 A | 1/1995 | Roger et al. |
| 5,147,362 A | 9/1992 | Goble | | 5,391,171 A | 2/1995 | Schmieding |
| 5,149,329 A | 9/1992 | Richardson | | 5,391,176 A | 2/1995 | de la Torre |
| 5,152,790 A | 10/1992 | Rosenberg et al. | | 5,393,302 A | 2/1995 | Clark et al. |
| 5,154,189 A | 10/1992 | Oberlander | | RE34,871 E | 3/1995 | McGuire et al. |
| 5,156,616 A | 10/1992 | Meadows et al. | | 5,397,356 A | 3/1995 | Goble et al. |
| 5,163,960 A | 11/1992 | Bonutti | | 5,403,328 A | 4/1995 | Shallman |
| D331,626 S | 12/1992 | Hayhurst et al. | | 5,403,329 A | 4/1995 | Hinchcliffe |
| 5,169,400 A | 12/1992 | Mühling et al. | | 5,403,348 A | 4/1995 | Bonutti |
| 5,176,682 A | 1/1993 | Chow | | 5,417,691 A | 5/1995 | Hayhurst |
| 5,178,629 A | 1/1993 | Kammerer | | 5,417,712 A | 5/1995 | Whittaker et al. |
| 5,183,458 A | 2/1993 | Marx | | 5,423,819 A | 6/1995 | Small et al. |
| 5,192,282 A | 3/1993 | Draenert | | 5,423,823 A | 6/1995 | Schmieding |
| 5,197,987 A | 3/1993 | Koch et al. | | 5,423,860 A * | 6/1995 | Lizardi et al. ............... 606/232 |
| 5,203,784 A | 4/1993 | Ross et al. | | 5,425,733 A | 6/1995 | Schmieding |
| 5,203,787 A | 4/1993 | Noblitt et al. | | 5,425,766 A | 6/1995 | Bowald |
| 5,207,679 A | 5/1993 | Li | | 5,433,751 A | 7/1995 | Christel et al. |
| 5,209,753 A | 5/1993 | Biedermann et al. | | 5,437,680 A | 8/1995 | Yoon |
| 5,209,805 A | 5/1993 | Spraggins | | 5,439,684 A | 8/1995 | Prewett et al. |
| 5,211,647 A | 5/1993 | Schmieding | | 5,443,468 A | 8/1995 | Johnson |
| 5,211,650 A | 5/1993 | Noda | | 5,443,482 A | 8/1995 | Stone et al. |
| 5,214,987 A | 6/1993 | Fenton, Sr. | | 5,443,483 A | 8/1995 | Kirsch |
| 5,219,359 A | 6/1993 | McQuilkin et al. | | 5,443,509 A | 8/1995 | Boucher et al. |
| 5,224,946 A | 7/1993 | Hayhurst et al. | | 5,445,833 A | 8/1995 | Badylak et al. |
| 5,230,699 A | 7/1993 | Grasinger | | 5,447,512 A | 9/1995 | Wilson et al. |
| 5,232,436 A | 8/1993 | Janevski | | 5,451,203 A | 9/1995 | Lamb |
| 5,234,435 A | 8/1993 | Seagrave, Jr. | | 5,454,811 A | 10/1995 | Huebner |
| 5,236,445 A | 8/1993 | Hayhurst et al. | | 5,456,685 A | 10/1995 | Huebner |
| 5,236,461 A | 8/1993 | Forte | | 5,456,722 A | 10/1995 | McLeod et al. |
| 5,242,447 A | 9/1993 | Borzone | | 5,458,601 A | 10/1995 | Young, Jr. et al. |
| 5,246,441 A | 9/1993 | Ross et al. | | 5,458,604 A | 10/1995 | Schmieding |
| 5,249,899 A | 10/1993 | Wilson | | 5,462,560 A | 10/1995 | Stevens |
| 5,258,015 A | 11/1993 | Li et al. | | 5,464,426 A | 11/1995 | Bonutti |
| 5,258,016 A | 11/1993 | DiPoto et al. | | 5,464,427 A | 11/1995 | Curtis et al. |
| 5,258,040 A | 11/1993 | Bruchman et al. | | 5,464,440 A | 11/1995 | Johansson et al. |
| 5,268,001 A | 12/1993 | Nicholson et al. | | 5,466,237 A | 11/1995 | Byrd, III et al. |
| 5,269,160 A | 12/1993 | Wood | | 5,467,786 A | 11/1995 | Allen et al. |
| 5,269,783 A | 12/1993 | Sander | | 5,470,334 A | 11/1995 | Ross et al. |
| 5,269,809 A | 12/1993 | Hayhurst et al. | | 5,470,337 A | 11/1995 | Moss |
| 5,281,422 A | 1/1994 | Badylak et al. | | 5,470,338 A | 11/1995 | Whitfield et al. |
| 5,282,809 A | 2/1994 | Kammerer et al. | | 5,472,452 A | 12/1995 | Trott |
| 5,282,832 A | 2/1994 | Toso et al. | | 5,474,565 A | 12/1995 | Trott |
| 5,285,040 A | 2/1994 | Brandberg et al. | | 5,474,568 A | 12/1995 | Scott |
| 5,290,217 A | 3/1994 | Campos | | 5,474,572 A | 12/1995 | Hayhurst |
| 5,306,301 A | 4/1994 | Graf et al. | | 5,478,344 A | 12/1995 | Stone et al. |
| 5,312,422 A | 5/1994 | Trott | | 5,478,345 A | 12/1995 | Stone et al. |
| 5,312,438 A | 5/1994 | Johnson | | 5,480,403 A | 1/1996 | Lee et al. |
| 5,318,577 A | 6/1994 | Li | | 5,480,406 A | 1/1996 | Nolan et al. |
| 5,318,578 A | 6/1994 | Hasson | | 5,484,442 A | 1/1996 | Melker et al. |
| 5,320,115 A | 6/1994 | Kenna | | 5,486,197 A | 1/1996 | Le et al. |
| 5,320,626 A | 6/1994 | Schmieding | | 5,490,750 A | 2/1996 | Gundy |
| 5,320,633 A | 6/1994 | Allen et al. | | 5,496,331 A | 3/1996 | Xu et al. |
| 5,324,308 A | 6/1994 | Pierce | | 5,496,348 A | 3/1996 | Bonutti |
| 5,334,204 A | 8/1994 | Clewett et al. | | 5,500,000 A | 3/1996 | Feagin et al. |
| 5,336,229 A | 8/1994 | Noda | | 5,505,736 A | 4/1996 | Reimels et al. |
| 5,336,231 A | 8/1994 | Adair | | 5,507,754 A | 4/1996 | Green et al. |
| 5,336,240 A | 8/1994 | Metzler et al. | | 5,520,691 A | 5/1996 | Branch |
| 5,342,369 A | 8/1994 | Harryman, II | | 5,520,702 A | 5/1996 | Sauer et al. |
| 5,346,462 A | 9/1994 | Barber | | 5,522,817 A | 6/1996 | Sander et al. |
| 5,354,298 A | 10/1994 | Lee et al. | | 5,522,820 A | 6/1996 | Caspari et al. |
| 5,356,413 A | 10/1994 | Martins et al. | | 5,522,844 A | 6/1996 | Johnson |
| 5,358,511 A | 10/1994 | Gatturna et al. | | 5,522,845 A | 6/1996 | Wenstrom, Jr. |

| Patent No. | Date | Inventor |
|---|---|---|
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,534,012 A | 7/1996 | Bonutti |
| 5,540,718 A | 7/1996 | Bartlett |
| 5,545,178 A * | 8/1996 | Kensey et al. ............... 606/213 |
| 5,545,228 A | 8/1996 | Kambin |
| 5,549,613 A | 8/1996 | Goble et al. |
| 5,549,617 A | 8/1996 | Green et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,305 A | 10/1996 | Bonutti |
| 5,571,090 A | 11/1996 | Sherts |
| 5,571,139 A | 11/1996 | Jenkins, Jr. |
| 5,573,286 A | 11/1996 | Rogozinski |
| 5,573,548 A | 11/1996 | Nazre et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Härle |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,352 A | 10/1997 | Clancy, III et al. |
| 5,683,419 A | 11/1997 | Thal |
| 5,688,285 A | 11/1997 | Yamada |
| 5,690,676 A | 11/1997 | DiPoto et al. |
| 5,690,678 A | 11/1997 | Johnson |
| 5,695,497 A | 12/1997 | Stahelin |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,718,717 A | 2/1998 | Bonutti |
| 5,720,765 A | 2/1998 | Thal |
| 5,720,766 A | 2/1998 | Zang et al. |
| 5,725,549 A | 3/1998 | Lam |
| 5,725,556 A | 3/1998 | Moser et al. |
| 5,725,581 A | 3/1998 | Brånemark |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,766,176 A | 6/1998 | Duncan |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,928 A | 8/1998 | Kogasaka |
| 5,800,407 A | 9/1998 | Eldor |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,860,973 A | 1/1999 | Michelson |
| 5,868,740 A | 2/1999 | LeVeen et al. |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |

| Patent | Date | Name |
|---|---|---|
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,267 A | 7/1999 | Bonutti et al. |
| 5,931,838 A | 8/1999 | Vito |
| 5,931,844 A | 8/1999 | Thompson et al. |
| 5,931,869 A | 8/1999 | Boucher et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,783 A | 10/1999 | Grafton et al. |
| 5,968,045 A | 10/1999 | Frazier |
| 5,968,047 A | 10/1999 | Reed |
| 5,976,125 A | 11/1999 | Graham |
| 5,976,127 A | 11/1999 | Lax |
| 5,980,524 A | 11/1999 | Justin et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,997,542 A | 12/1999 | Burke |
| 5,997,552 A | 12/1999 | Person et al. |
| 6,001,100 A | 12/1999 | Sherman et al. |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,033,430 A | 3/2000 | Bonutti |
| 6,039,753 A | 3/2000 | Meislin |
| 6,042,601 A | 3/2000 | Smith |
| 6,045,551 A | 4/2000 | Bonutti |
| 6,045,571 A | 4/2000 | Hill et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,053,916 A | 4/2000 | Moore |
| 6,056,752 A | 5/2000 | Roger et al. |
| 6,056,772 A | 5/2000 | Bonutti |
| 6,056,773 A | 5/2000 | Bonutti |
| 6,059,817 A | 5/2000 | Bonutti et al. |
| 6,062,344 A | 5/2000 | Okabe et al. |
| 6,068,648 A | 5/2000 | Cole et al. |
| 6,074,403 A | 6/2000 | Nord |
| 6,077,277 A | 6/2000 | Mollenauer et al. |
| 6,077,292 A | 6/2000 | Bonutti |
| 6,086,591 A | 7/2000 | Bojarski |
| 6,086,592 A | 7/2000 | Rosenberg et al. |
| 6,086,608 A | 7/2000 | Ek et al. |
| 6,096,060 A | 8/2000 | Fitts et al. |
| 6,099,530 A | 8/2000 | Simonian et al. |
| 6,099,568 A | 8/2000 | Simonian et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,187,025 B1 | 2/2001 | Machek |
| 6,190,401 B1 | 2/2001 | Green et al. |
| 6,190,411 B1 | 2/2001 | Lo |
| 6,193,754 B1 | 2/2001 | Seedhom et al. |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,283,973 B1 | 9/2001 | Hubbard et al. |
| 6,283,996 B1 | 9/2001 | Chervitz et al. |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,398,785 B2 | 6/2002 | Carchidi et al. |
| 6,409,743 B1 | 6/2002 | Fenton, Jr. |

| | | |
|---|---|---|
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 * | 11/2002 | Johnson et al. .............. 606/216 |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thai |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Järvinen |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,572,655 B1 | 6/2003 | Johnson |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 12/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B2 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,972,027 B2 | 12/2005 | Fallin et al. |
| 6,986,781 B2 | 1/2006 | Smith |
| 6,989,034 B2 | 1/2006 | Hammer et al. |
| 7,066,944 B2 | 6/2006 | Laufer et al. |
| 7,105,010 B2 | 9/2006 | Hart et al. |
| 7,112,221 B2 | 9/2006 | Harris et al. |

| | | |
|---|---|---|
| 7,118,583 B2 | 10/2006 | O'Quinn et al. |
| 7,137,996 B2 | 11/2006 | Steiner et al. |
| 7,141,066 B2 | 11/2006 | Steiner et al. |
| 7,153,312 B1 | 12/2006 | Torrie et al. |
| 7,261,716 B2 | 8/2007 | Strobel et al. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0019649 A1 | 2/2002 | Sikora et al. |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120270 A1* | 8/2002 | Trieu et al. .................... 606/61 |
| 2002/0120292 A1 | 8/2002 | Morgan |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0169452 A1 | 11/2002 | Tormala et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078617 A1 | 4/2003 | Schwartz et al. |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1 | 7/2003 | Bojarski et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown, Jr. et al. |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0111117 A1 | 6/2004 | Colleran et al. |
| 2004/0122431 A1 | 6/2004 | Biedermann et al. |
| 2004/0138664 A1 | 7/2004 | Bowman |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya |
| 2004/0182968 A1* | 9/2004 | Gentry .................... 244/155 A |
| 2004/0220574 A1 | 11/2004 | Pelo et al. |
| 2004/0225292 A1 | 11/2004 | Sasso et al. |
| 2004/0236353 A1 | 11/2004 | Bain et al. |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0064042 A1 | 3/2005 | Vunjak-Novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | McGuire et al. |
| 2005/0159812 A1 | 7/2005 | Dinger, III et al. |
| 2005/0165416 A1 | 7/2005 | Bojarski et al. |
| 2005/0165482 A1 | 7/2005 | Goldhahn et al. |
| 2005/0222618 A1 | 10/2005 | Dreyfuss et al. |
| 2005/0222619 A1 | 10/2005 | Dreyfuss et al. |
| 2005/0228448 A1* | 10/2005 | Li .................... 606/232 |
| 2005/0267479 A1 | 12/2005 | Morgan et al. |
| 2005/0277961 A1 | 12/2005 | Stone et al. |
| 2005/0283156 A1 | 12/2005 | Schmieding et al. |
| 2005/0283158 A1 | 12/2005 | West |
| 2005/0283192 A1* | 12/2005 | Torrie et al. .................... 606/228 |
| 2006/0030948 A1 | 2/2006 | Manrique et al. |
| 2006/0036265 A1 | 2/2006 | Dant |
| 2006/0064126 A1 | 3/2006 | Fallin et al. |
| 2006/0069334 A1 | 3/2006 | Moskowitz |
| 2006/0100627 A1 | 5/2006 | Stone et al. |
| 2006/0121084 A1 | 6/2006 | Borden et al. |
| 2006/0135958 A1 | 6/2006 | Marissen et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0229671 A1 | 10/2006 | Steiner et al. |
| 2006/0247642 A1 | 11/2006 | Stone et al. |
| 2006/0271192 A1 | 11/2006 | Olsen et al. |
| 2006/0280768 A1 | 12/2006 | Hwang et al. |
| 2006/0282085 A1 | 12/2006 | Stone et al. |
| 2006/0293709 A1 | 12/2006 | Bojarski et al. |
| 2007/0016305 A1 | 1/2007 | Chudik |
| 2007/0055255 A1 | 3/2007 | Siegel |
| 2007/0078435 A1 | 4/2007 | Stone et al. |
| 2007/0083236 A1 | 4/2007 | Sikora et al. |
| 2008/0027446 A1 | 1/2008 | Stone et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0255613 A1 | 10/2008 | Kaiser et al. |

| | | |
|---|---|---|
| 2008/0312689 A1 | 12/2008 | Denham et al. |
| 2009/0054928 A1 | 2/2009 | Denham et al. |
| 2009/0062854 A1 | 3/2009 | Kaiser et al. |
| 2009/0082805 A1 | 3/2009 | Kaiser et al. |
| 2009/0192468 A1 | 7/2009 | Stone |

FOREIGN PATENT DOCUMENTS

| | | |
|---|---|---|
| AU | 4402/66 | 4/1966 |
| AU | 22237/67 | 11/1968 |
| AU | 50285/69 | 8/1970 |
| AU | 58504/69 | 1/1971 |
| AU | 59638/69 | 2/1971 |
| AU | 15054/70 | 11/1971 |
| AU | 36151/71 | 5/1973 |
| AU | 43812/68 | 9/1973 |
| AU | A-71108/87 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 29 19 009 C2 | 11/1979 |
| DE | 3027138 | 12/1981 |
| DE | 3225620 A1 | 2/1983 |
| DE | 3136083 | 3/1983 |
| DE | 233 303 A1 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 A2 | 5/1984 |
| EP | 0 129 422 | 12/1984 |
| EP | 0129442 | 12/1984 |
| EP | 0172130 | 2/1986 |
| EP | 0 241 240 | 10/1987 |
| EP | 0241792 | 10/1987 |
| EP | 0260970 A2 | 3/1988 |
| EP | 0270704 | 6/1988 |
| EP | 0282789 | 9/1988 |
| EP | 0315371 A2 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0 415 915 | 3/1991 |
| EP | 0 440 991 | 8/1991 |
| EP | 0 441 065 | 8/1991 |
| EP | 0451932 | 10/1991 |
| EP | 0464480 | 1/1992 |
| EP | 0 490 417 A1 | 6/1992 |
| EP | 0497079 | 8/1992 |
| EP | 0 502 698 | 9/1992 |
| EP | 0502509 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 A2 | 5/1994 |
| EP | 0627203 | 12/1994 |
| EP | 0 651 979 | 5/1995 |
| EP | 0 669 110 | 8/1995 |
| EP | 0 686 373 | 12/1995 |
| EP | 0702933 | 3/1996 |
| EP | 0 775 473 | 5/1997 |
| EP | 0 913 131 | 5/1999 |
| EP | 0913123 A1 | 5/1999 |
| EP | 99 121 052.7 | 10/1999 |
| EP | 99 121 106 | 10/1999 |
| EP | 0 995 409 | 4/2000 |
| EP | 1013229 A2 | 6/2000 |
| EP | 1 093 774 | 4/2001 |
| EP | 1093773 | 4/2001 |
| EP | 1555945 | 7/2005 |
| FR | 2622790 | 12/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2 083 751 | 3/1982 |
| GB | 2 118 474 | 11/1983 |
| GB | 2227175 | 7/1990 |
| GB | 2253147 | 9/1992 |
| GB | 2 312 376 | 10/1997 |
| JP | 53-62911 | 5/1978 |
| JP | 53-62912 | 5/1978 |
| JP | 53-74942 | 6/1978 |
| JP | 53-78230 | 6/1978 |
| JP | 54-166092 | 11/1979 |
| JP | 54-166093 | 11/1979 |
| JP | 54-176284 | 12/1979 |
| JP | 54-178988 | 12/1979 |
| JP | 62-159647 | 7/1987 |
| JP | 62295657 | 12/1987 |
| JP | 5269160 | 10/1993 |
| JP | 5300917 | 11/1993 |
| JP | 7-51292 | 2/1995 |
| JP | 10-211213 | 8/1998 |
| WO | WO 83/00615 | 3/1983 |
| WO | WO 86/03666 | 7/1986 |
| WO | WO 87/01270 | 3/1987 |
| WO | WO-8901767 | 3/1989 |
| WO | WO-8909030 | 10/1989 |
| WO | WO 89/10096 | 11/1989 |
| WO | WO-9008510 | 8/1990 |
| WO | WO-9203980 | 3/1992 |
| WO | WO 93/15694 | 8/1993 |
| WO | WO-9314705 | 8/1993 |
| WO | WO 95/02373 | 1/1995 |
| WO | WO-9529637 | 11/1995 |
| WO | WO-9532670 | 12/1995 |
| WO | WO-9629029 | 9/1996 |
| WO | WO 97/37603 | 10/1997 |
| WO | WO-9812991 | 4/1998 |
| WO | WO-9812992 | 4/1998 |
| WO | WO 98/22048 | 5/1998 |
| WO | WO 9822047 | 5/1998 |
| WO | WO 9901084 | 1/1999 |
| WO | WO 9912480 | 3/1999 |
| WO | WO 99/44544 | 9/1999 |
| WO | WO 00/40159 | 7/2000 |
| WO | WO 0139671 A1 | 6/2001 |
| WO | WO 0236020 | 5/2002 |
| WO | WO 03/071962 A2 | 9/2003 |
| WO | WO 03/077772 A1 | 9/2003 |
| WO | WO 2005/104992 | 11/2005 |

OTHER PUBLICATIONS

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

F. Alan Barber, M.D., "Using Sutures and Anchors," San Diego Shoulder Arthroscopy Course, 17th Annual Meeting.

Hecker AT, et al., "Pull-out strength of suture anchors for rotator cuff and Bankart lesion repairs," Am J Sports Med. 1993.

Flavia Namie Azato, et al. "Traction endurance biomechanical study of metallic suture anchors at different insertion angles," Acta ortop. bras., vol. 11, No. 1, Sao Paulo, Jan./Mar. 2003.

F. Alan Barber, M.D., "Uses and Abuses of Sutures and Anchors," Shoulder Scope, San Diego Shoulder Arthroscopy Library.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

Opus Medical; The AutoCuff System; www.opusmedical.com.; 2003.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

Mark D. Miller et al.; "Pitfalls Associated with FasT-Fix Meniscal Repair," Arthroscopy: The Journal of Arthroscopic and Related Surgery, vol. 18, No. 8 (October), 2002: pp. 939-943.

Roy Alan Majors, M.D.; "Meniscal repairs: proven techniques and current trends," Lippincott Williams & Wilkins, Inc.; 2002.

Shoulder Arthroscopy; pp. H-2-H-22.

"EZ Loc Femoral Fixation Device," copyright 2005 Arthrotek, Inc. (8 sheets).

"Panalok Anchor with PDS II and Ethibond Suture", Mitek Products ETHICON, 1997.

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

Lawhorn, M.D., Keith, MaxFire™ Meniscal Repair Device with Zip Loop™ Technology, Biomet Sports Medicine, Feb. 29, 2008.

ToggleLoc™ Femoral Fixation Device, Arthrotek, Mar. 31, 2006.

US 6,238,418, 05/2001, Schwartz et al. (withdrawn)

* cited by examiner

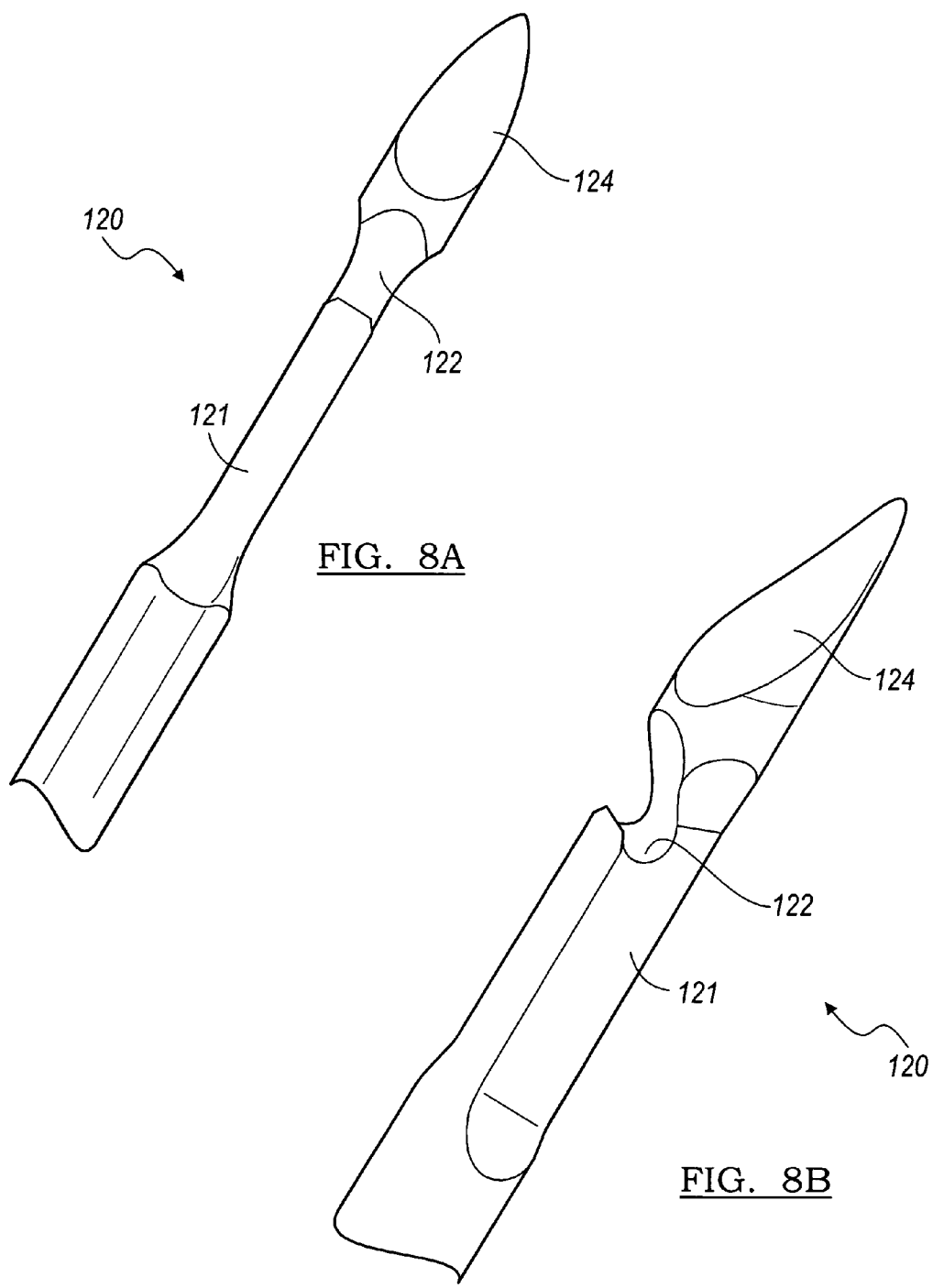

SOFT TISSUE REPAIR ASSEMBLY AND ASSOCIATED METHOD

INTRODUCTION

Tears caused by trauma or disease in soft tissue, such as cartilage, ligament, or muscle, can be repaired by suturing. Various assemblies have been developed for facilitating suturing and are effective for their intended purposes. Nevertheless, tissue repair assemblies for facilitating suturing are still desirable.

SUMMARY

The present teachings provide a soft tissue repair assembly. The assembly includes a flexible member having first and second ends, and a flexible strand passing through the flexible member. The strand has first and second strand ends extending through the flexible member, such that pulling at least one of the first and second strand ends changes the flexible member from a first shape suitable for insertion through soft tissue to a second shape suitable for securely lodging the soft tissue repair assembly relative to soft tissue.

The present teachings provide a soft tissue repair assembly that includes an inserter, at least one flexible member preloaded on the inserter in a first shape, and a flexible strand coupled to the flexible member for changing the shape of the flexible member from the first shape to a second shape after implantation, wherein the second shape is suitable for securely lodging the flexible member relative to soft tissue.

The present teachings provide a method for repairing a tear in soft tissue. The method includes preloading a flexible member coupled to a flexible strand on an inserter, inserting the inserter through tissue from a first side of the tear to a second side of the tear, and deploying the flexible member relative to the soft tissue. The method further includes tensioning the strand, changing the shape of the flexible member from a first shape to a second shape suitable for securely lodging the flexible member relative to the soft tissue, and reducing or closing the tear.

The present teachings provide a method for repairing a tear in a meniscus during arthroscopic knee procedure. The method includes inserting an inserter through the tear to an outer surface of the meniscus, deploying a first flexible member coupled to a flexible strand from the inserter on an outer surface of the meniscus, tensioning the strand, changing the shape of the first flexible member from a first shape to a second shape for securing the flexible member on the outer surface, and reducing or closing the tear.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 8A is a plan view of an inserter according to the present teachings;

FIG. 8B is a side view of the inserter of FIG. 8A;

DESCRIPTION OF VARIOUS ASPECTS

The following description is merely exemplary in nature and is in no way intended to limit the invention, its application, or uses. For example, although the present teachings are illustrated in an application for meniscus repair in knee surgery, the present teachings can also be used for repairing any tissue, such as bone, muscle, ligament or tendon in an arthroscopic or other open procedure.

Figure 1:
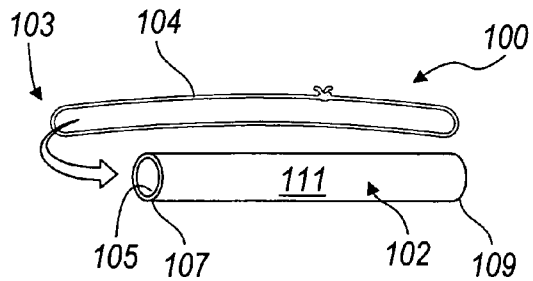
FIG. 1 is an exploded view of a soft-tissue repair assembly according to the present teachings.
Figure 7A:
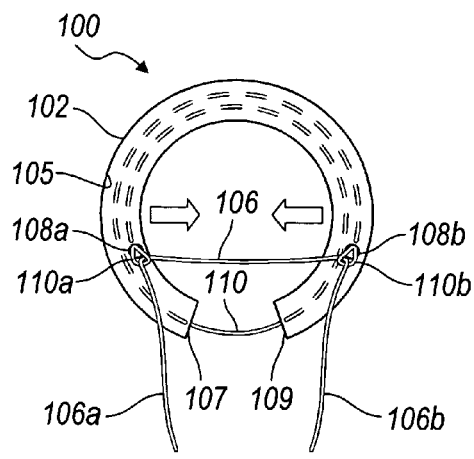
FIG. 7A is a plan view of a soft-tissue repair assembly according to the present teachings, shown in a first shape.
Figure 7B:
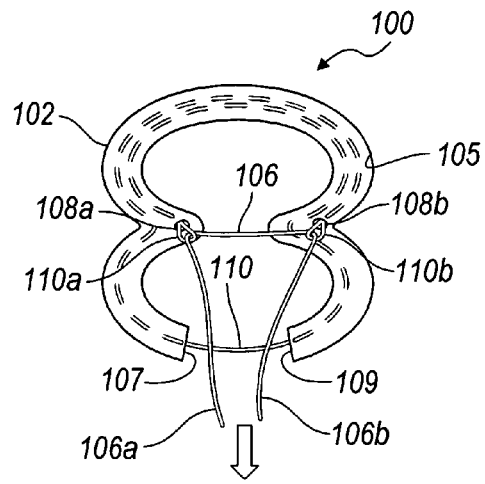
FIG. 7B is a plan view of the soft-tissue repair assembly of FIG. 7A, shown in a second shape.
Figure 7C:
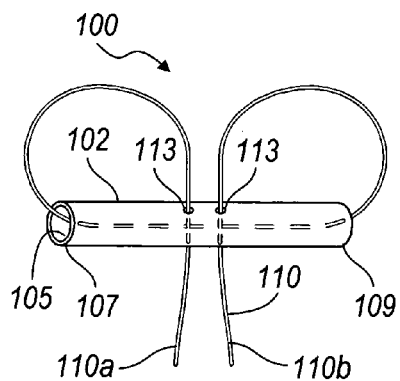
FIG. 7C is a plan view of a soft-tissue repair assembly according to the present teachings, shown in a first shape.
Figure 7D:
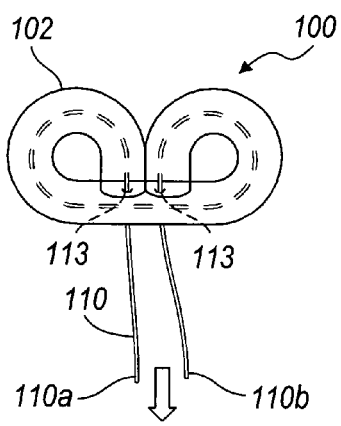
FIG. 7D is a plan view of the soft-tissue repair assembly of FIG. 7C, shown in a second shape.
Figure 7E:
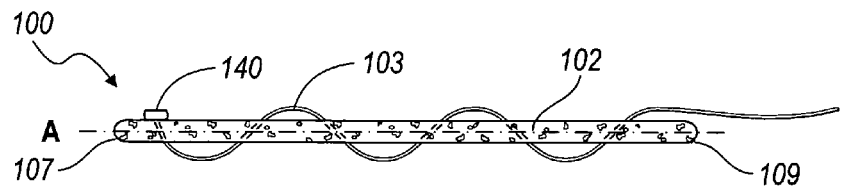
FIG. 7E is a plan view of a soft-tissue repair assembly according to the present teachings, shown in a first shape.

Referring to FIG. 1 and FIG. 7E, an exemplary soft tissue repair assembly 100 according to the present teachings can include a flexible member 102, and a flexible strand 103, such as, for example, thread, ligament, wire, or suture. The strand 103 can be coupled with the flexible member 102 for changing the shape of the flexible member 102. The flexible member 102 can be an elongated member having first and second ends 107, 109. The elongated member can include a substantially cylindrical wall 111 having a longitudinal bore 105, as illustrated in FIG. 1, or can be a flexible elongated solid member 102 with a bore, as illustrated in FIG. 7E, or any other shape. The flexible member 102 can be made of resorbable or non-resorbable materials, including sponges and sponge-like materials in solid form, perforated materials, woven/braided from biocompatible materials or fibers, such as, for example, polymer, polyester, polyethylene, cotton, silk, or other natural or synthetic materials, include sponges and sponge-like materials. The flexible member 102 can also be an elongated tubular or solid member or a two-dimensional member with or without internal bores. The flexible member 102 can have any properties that allow the flexible member 102 to change shape. The flexible member 102 can be, for example, compliant, flexible, foldable, squashable, squeezable, deformable, limp, flaccid, elastic, low-modulus, soft, spongy, perforated or any other flexible member which can change shape. In some aspects, the flexible member 102 can be coated with biological or biocompatible coatings, and it can also be soaked in platelets and other biologics, which can be easily absorbed by the flexible member 102 in particular when, for example, the flexible member 102 is made from spongy, absorbent material.

Referring to FIGS. 1-4, the flexible strand 103 can include an inner loop portion 104 and outer strand portion 106. The inner loop portion 104 can be substantially contained within the bore 105, such that the inner loop portion 104 extends from the first end 107 of the bore 105, passes through the bore 105, and terminates at the second end 109 of the bore 105. The outer strand portion 106 can be coupled to the loop portion 104 adjacent the first and second ends 107, 109 and can extend substantially outside the flexible member 102.

Figure 3:
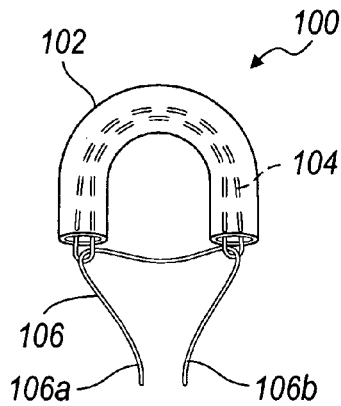
FIG. 3 is a perspective view of the soft-tissue repair assembly of FIG. 2, shown in a second shape.
Figure 2:
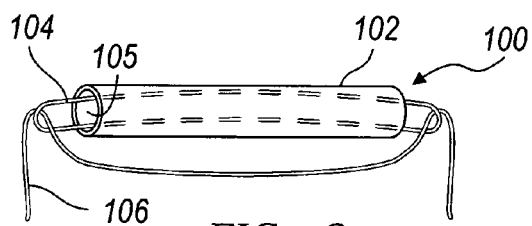
FIG. 2 is a perspective view of a soft-tissue repair assembly according to the present teachings, shown in a first shape.
Figure 4:
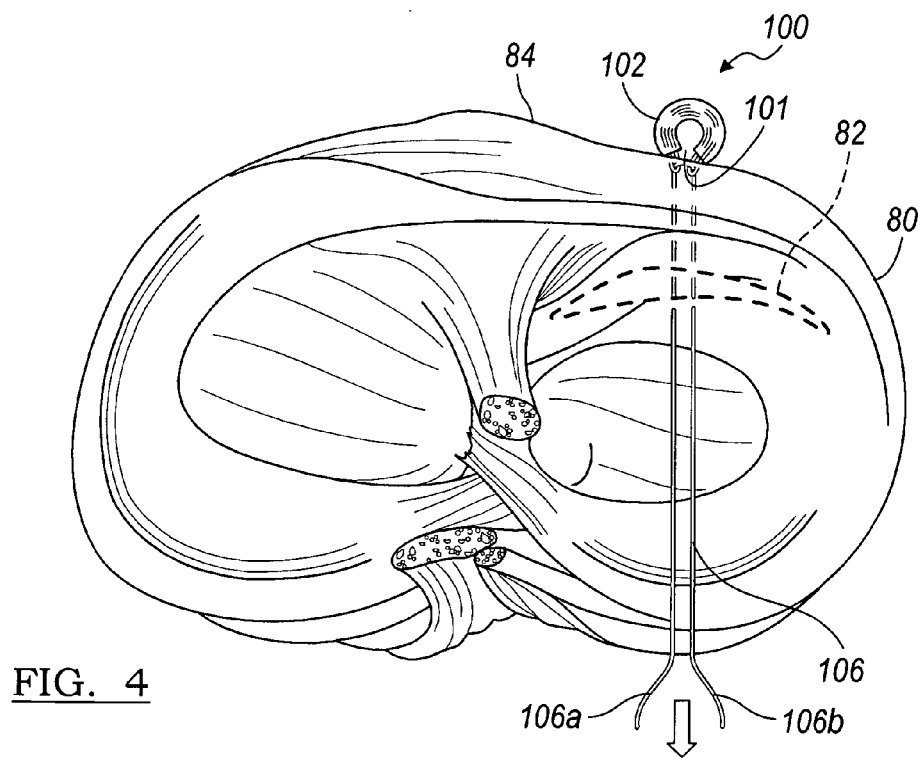
FIG. 4 is an environmental view of the soft-tissue repair assembly of FIG. 2, shown implanted relative to soft tissue.

The strand 103 can be made of braided filaments or fibers of biocompatible material, including natural and synthetic fibers, such as cofton, silk, polymer, polyester, polyethylene, and other materials. The inner loop portion 104 can be knotted, as shown in FIG. 1, or continuous, as shown in FIG. 2. The outer strand portion 106 can be a separate piece of strand 103 and can include first and second ends 106a, 106b. Pulling at the ends 106a, 106b, or at least one of the ends 106a, 106b while holding the other end fixed, when the flexible member 102 is implanted relative to soft tissue or on an outer surface of soft tissue causes the flexible member 102 to change shape from a first shape to a second or implanted shape. The first shape of the flexible member 102 can be a thin elongated shape with length to width (aspect ratio) greater than one. The first shape of the flexible member 102 can also be a folded shape. The implanted shape of the flexible member 102 can be a bulkier shape with length to width ratio close to one, as illustrated in FIGS. 3 and 4, for snugly securing the flexible member 102 relative to or on an outer surface of soft tissue 80. The implanted shape of the flexible member 102 can have bigger overall width or enclosed cross-sectional area or volume than those of the first shape such that the flexible member 102 cannot be pulled out of the same opening through which it was originally inserted. In one aspect, the flexible member 102 can retain its bulkier shape after implantation, even after the tension on the strand portion 106 is removed.

Figure 5:
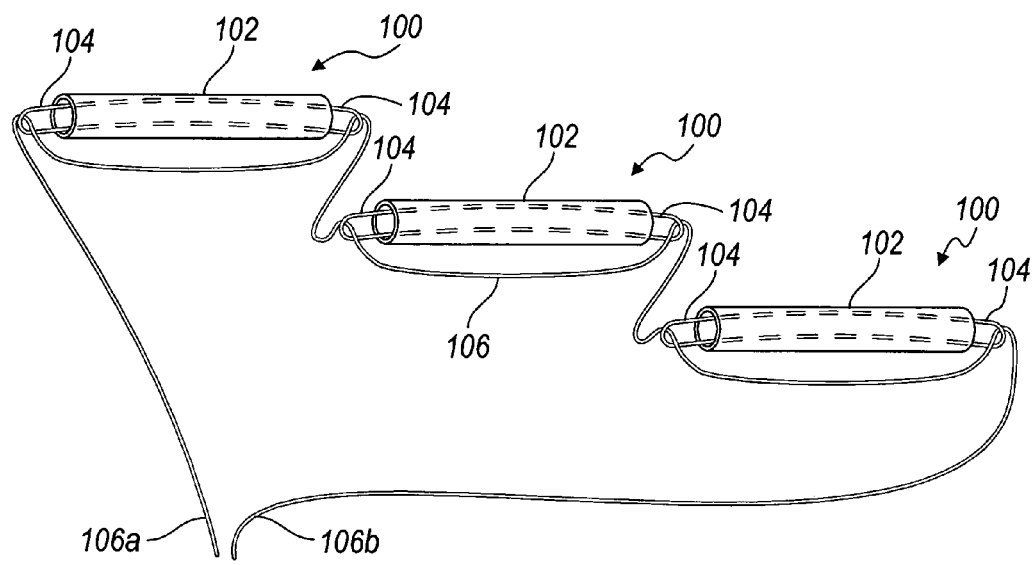
FIG. 5 is a perspective view of a plurality of connected soft-tissue repair assemblies according to the present teachings shown in first shapes.
Figure 6:
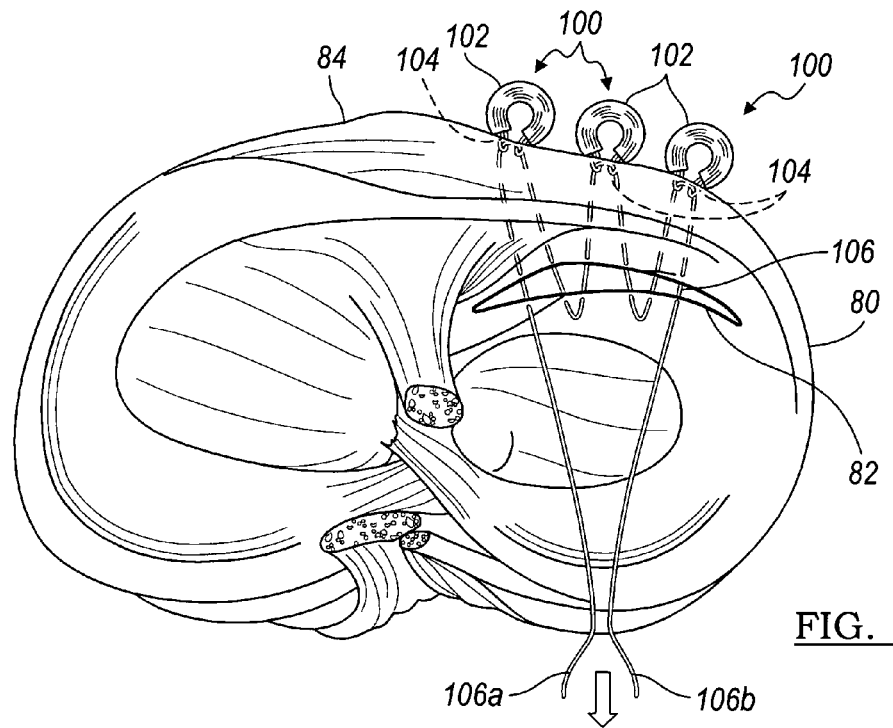
FIG. 6 is an environmental view of the soft-tissue repair assemblies of FIG. 5, shown in second shapes and implanted relative to soft tissue.

In the exemplary illustration of FIG. 4, the soft-tissue repair assembly 100 is shown implanted on an outer surface 84, such as a posterior surface of a meniscal soft tissue 80, after passing through a tear 82 for reducing or closing the tear 82. In FIG. 4, the suture securing second shape of the flexible member 102 is substantially a circular shape, but having a slit or gap 101. Referring to FIGS. 5 and 6, multiple soft tissue repair assemblies 100 can be daisy-chained together by a single continuous outer strand portion 106 connected to each inner loop portion 104 for reducing the tear 82. Generally, the soft-tissue repair assembly 100 can be positioned relative to soft tissue, such as in the soft tissue, adjacent the soft tissue, or on an outer surface of the soft tissue.

Referring to FIG. 7A, a continuous strand 110 can be used to define an inner loop having an outer portion and loop ends 110a, 110b. After the strand 110 is looped around the bore 105 of the flexible member 102, such that the first and second ends 107, 109 of the flexible member 102 are coupled by the outer portion of the strand 110, the loop ends 110a, 110b of the continuous strand 110 exit the bore 105 through small wall openings 108a, 108b adjacent but displaced from the ends 107, 109 of the flexible member 102. A second strand 106 having ends 106a, 106b is looped around the loop ends 110a, 110b. Pulling the ends 106a, 106b, of the second strand 106 causes the flexible member 102 to change shape to an eight-like securing shape, which appears pinched in the vicinity of the openings 108a, 108b, as illustrated in FIG. 7B. The eight-like shape of the flexible member 102 provides a geometry that encloses bigger area or volume for the same length of flexible member. Bigger securing volume can prevent the flexible member 102 from being pulled out of the insertion opening, and can provide secure and strong anchoring in various applications at the discretion of the surgeon.

Referring to FIGS. 7C and 7D, a continuous strand 110 can be passed through the bore 105 of the flexible member 102, such the strand ends 110a, 110b exit through wall openings 113 defined away from the flexible member ends 107, 109, in a middle section of the flexible member 102, such that pulling the strand ends 110a, 110b away from the flexible member 102, causes the flexible member 102 to change shape into a pretzel-like securing shape, which can be selected for application when bigger enclosed area/volume is desired for the same length of flexible member 102. It will be appreciated that the wall openings 113, as well as the wall openings 108a, 108b discussed above in connection with FIGS. 7A, 7B, do not need to be preformed holes. The wall openings 113, 108a, 108b, can be for example, space between fibers when the flexible member is woven or braided. The strand 110 can be passed through the wall 111 or between woven/braided fibers of the flexible member 102 using a suture threader, for example, or other instrument. The wall openings 108a, 108b and 113 can allow the flexible member 102 to slide relatively freely along at least a portion of the strand 110, thereby helping to position the strand 110 before changing the shape of the flexible member 102 to the final implantation and suture securing shape.

It will be appreciated that various soft-tissue suture securing shapes, including those described above as well as other shapes, can be used with the same flexible member 102 by varying the manner of looping the strand or strand portions or separate strands relative to the flexible member 102, and varying the number and/or location of various openings, such as the openings 108a, 108b, 113 described above, for producing a desired suture-securing shape. Generally, the suture-securing shapes have a bulky shape and occupy a greater volume for securing the flexible member 102 snuggly into soft tissue. Furthermore, the flexible member 102 lacks any sharp or cutting elements, sharp points, edges, or planes, such as barbs, hooks, fins, pins, threads, ribs, or other tissue-piercing features, generally associated sharp-element anchoring. Accordingly, the soft tissue repair assembly 102, in its various shapes, does not pierce or cut or otherwise injure soft tissue, and does not rely on sharp-element anchoring for securing suture into soft tissue. On the contrary, the soft-tissue repair assembly 100 provides suture securing that can be effected by changing the shape of the flexible member 102 into a bulkier second shape, which is relatively smooth and lacks any sharp elements or geometric features. In the bulkier shape the flexible member 102 can be lodged tightly outside soft tissue, or in or between layers of soft tissue, possibly displacing soft tissue, but without piercing, cutting or otherwise damaging soft tissue. In the bulkier shape, the flexible member 102 can be prevented from backing out of the original insertion opening, or tearing through tissue.

Figure 7F:
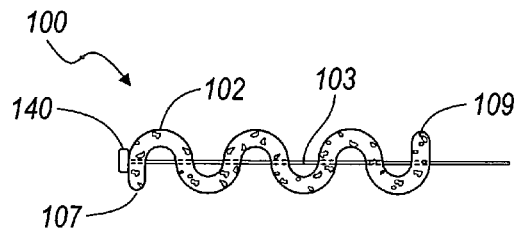
FIG. 7F is a plan view of the soft-tissue repair assembly of FIG. 7A, shown in a second shape.
Figure 7G:
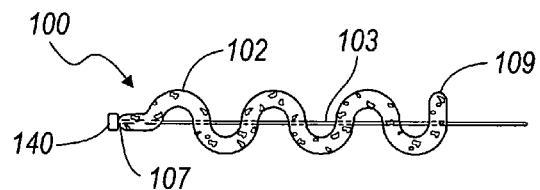
FIG. 7G is a plan view of a soft-tissue repair assembly according to the present teachings.

Referring to FIGS. 7E-7G, the elongated flexible member 102 can be coupled with a flexible strand 103 which can be retained with a button or knot or other retainer 140 adjacent a first end 107 of the flexible member 102 and then threaded in and out of the flexible member 102 along a longitudinal axis A of the flexible member 102 exiting adjacent a second end 109 of the flexible member 102. Pulling the strand 103 away from the retainer 140 can cause the flexible member 102 to scrunch up against the retainer 140 in a wavy, zigzag, multi-fold or accordion-like fashion, as illustrated in FIGS. 7F and 7G. The flexile member 102 can have a solid or annular cross-section.

Figure 7H:
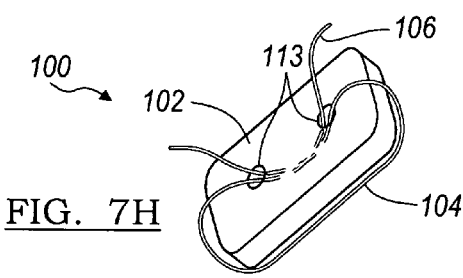
FIG. 7H is a plan view of a soft-tissue repair assembly according to the present teachings, shown in a first shape.
Figure 7I:
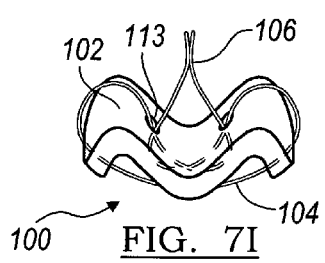
FIG. 7I is a plan view of the soft-tissue repair assembly of FIG. 7H, shown in a second shape.
Figure 7J:
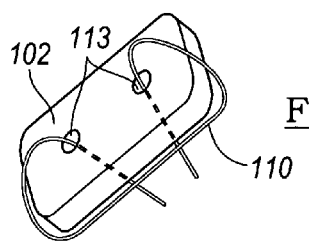
FIG. 7J is a plan view of a soft-tissue repair assembly according to the present teachings.
Figure 7K:
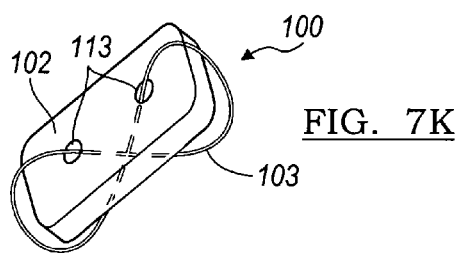
FIG. 7K is a plan view of a soft-tissue repair assembly according to the present teachings.
Figures 9A, 9B:
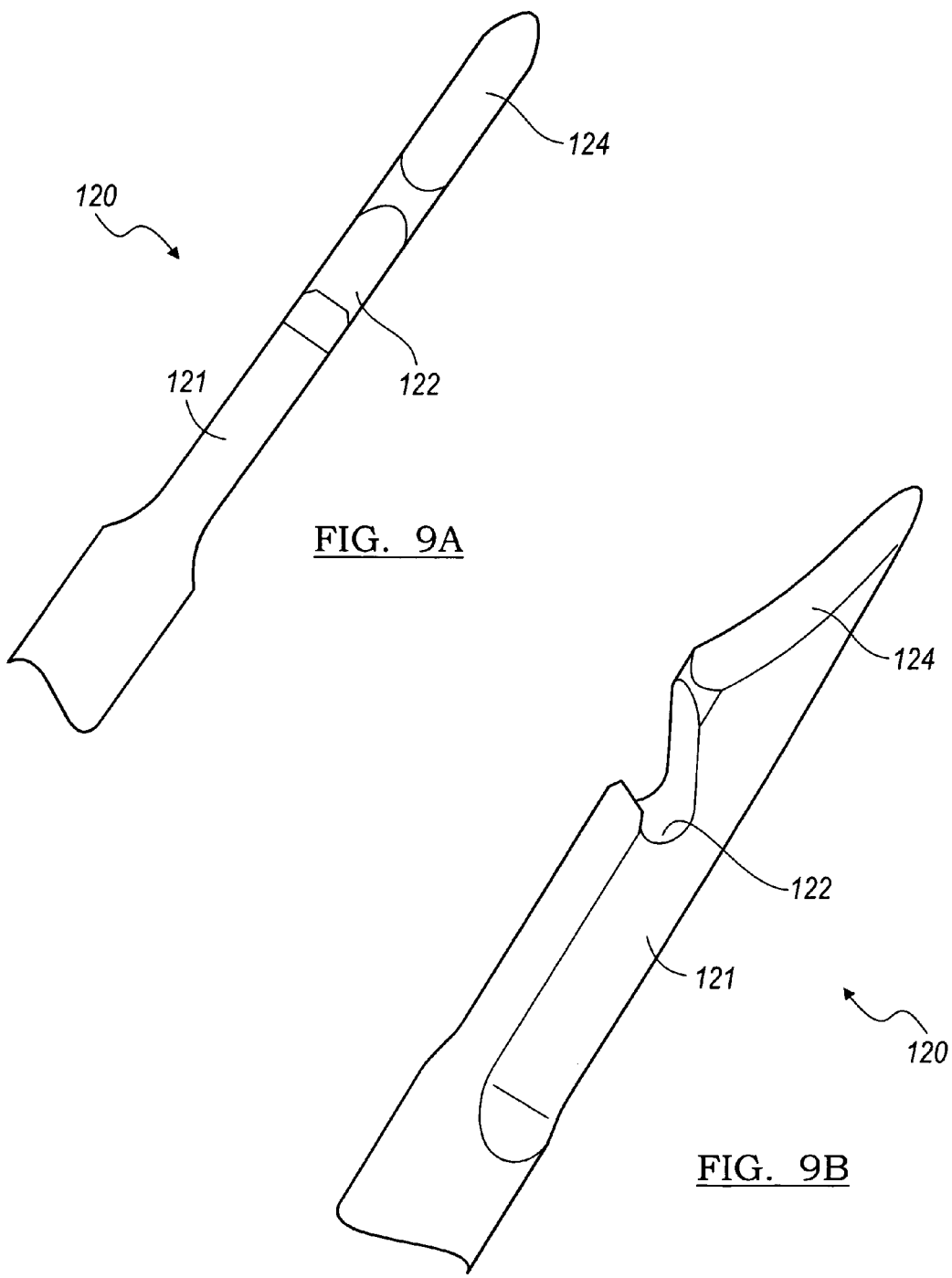
FIG. 9A is a plan view of an inserter according to the present teachings.
FIG. 9B is a side view of the inserter of FIG. 9A.

Referring to FIGS. 7H-7K, the flexible member 102 can have a substantially flat, planar or generally two-dimensional shape, formed, for example, as a flat sponge or a piece of woven fabric or other flaccid material which can be pierced for passing a single strand 110 therethrough, as illustrated in FIG. 7J, or for passing a strand loop 104 coupled with an open strand 106, as illustrated in FIG. 7H. A piece of strand 103 can be passed through the flexible member 102 in various other configurations, including, for example, the configuration illustrated in FIG. 9K. Pulling at least one the strand 103, 106, 110 can cause the flexible member 102 to change shape. FIG. 7I, for example, illustrates the new shape of the flexible member 102 of FIG. 7H, after tensioning the strand 106.

Figure 14:
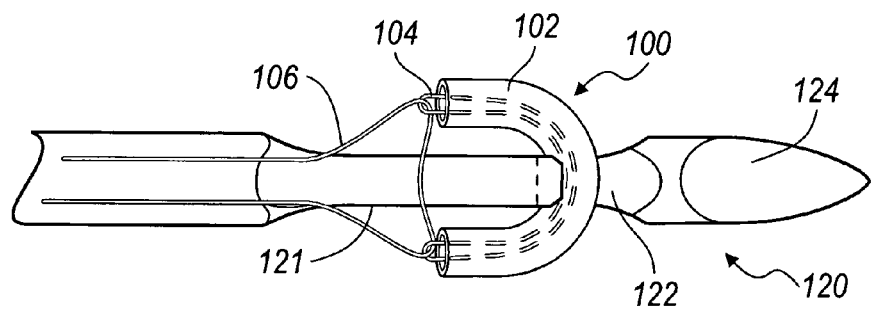
FIG. 14 is a plan view of an inserter shown holding a soft-tissue repair assembly according to the present teachings.
Figure 15:
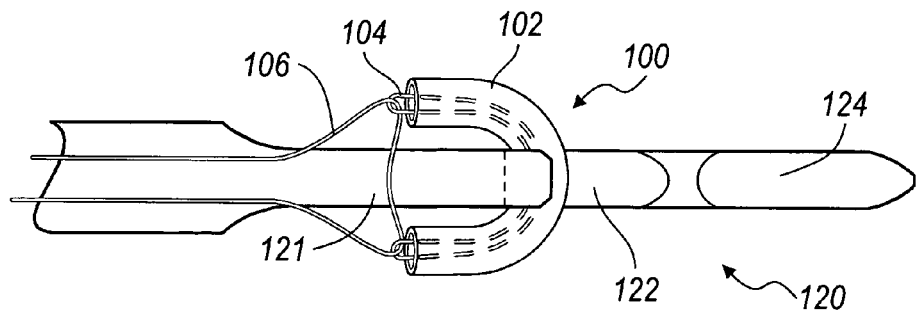
FIG. 15 is a plan view of an inserter shown holding a soft-tissue repair assembly according to the present teachings.

Referring to FIGS. 8A-15, various instruments can be used for implanting one or more soft tissue assemblies 100 relative to soft tissue. FIGS. 8A, 8B and 14 illustrate an inserter 120 having a rounded angled tip surface 124 and a shaft 121 defining a cutout or groove 122. The groove 122 can be configured for supporting a single flexible member 102 in a bent or folded shape draped over the groove 122, as illustrated in FIG. 14. FIGS. 9A, 9B and 15, illustrate a similar inserter 120 having a substantially rectangular angled tip surface 124. A sleeve 125 can be placed over the flexible member 102 to protect and keep the flexible member 102 and the strand 106 on the inserter 120, as illustrated in FIG. 15.

Figure 10:
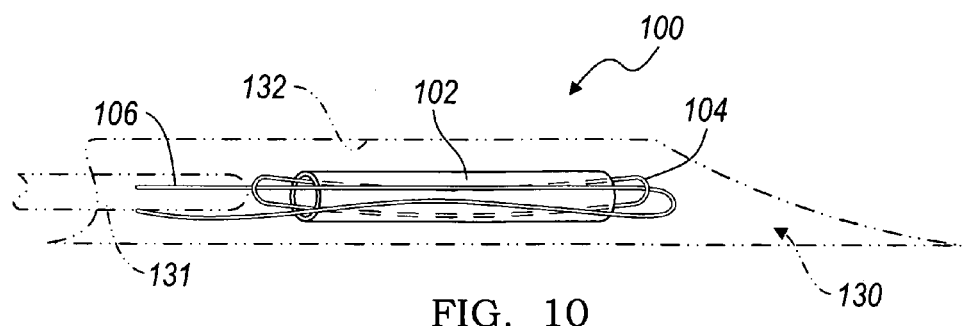
FIG. 10 is a side view of an inserter shown holding a soft-tissue repair assembly according to the present teachings.
Figure 10A:
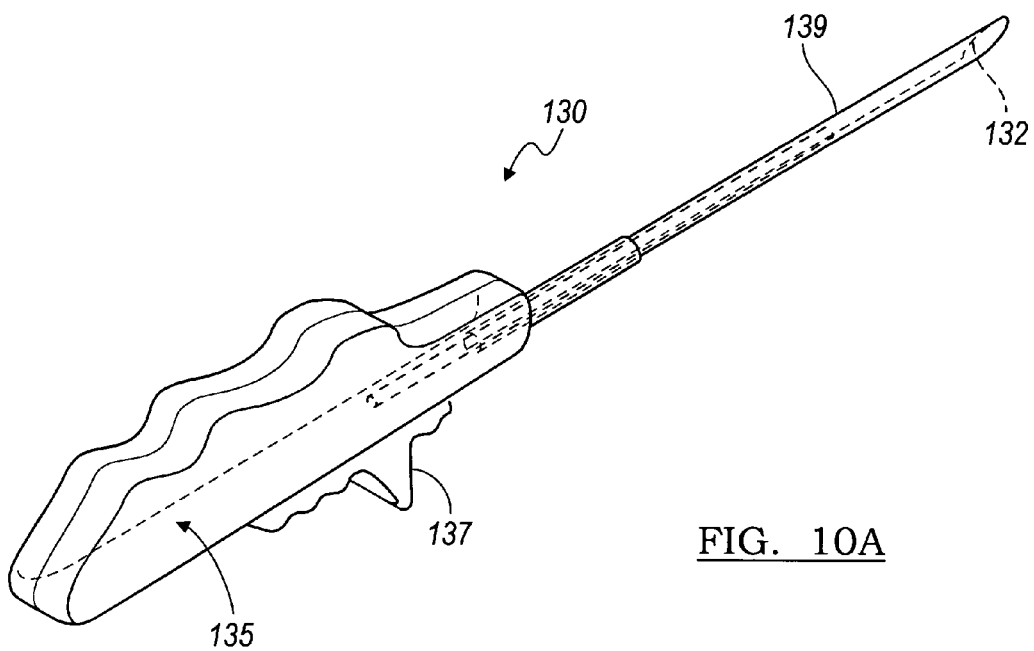
FIG. 10A is a perspective view of an exemplary inserter, according to the present teachings.
Figure 11:
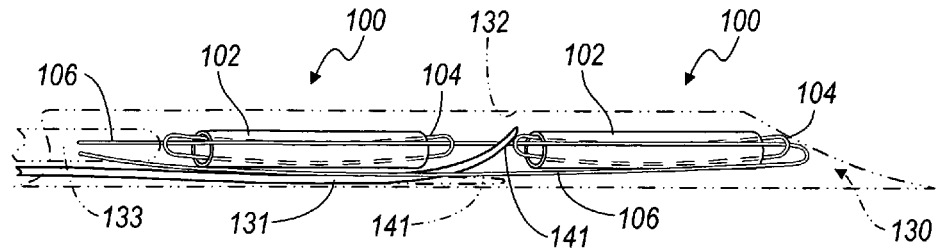
FIG. 11 is a side view of an inserter shown holding two soft-tissue repair assemblies according to the present teachings.
Figure 11A:
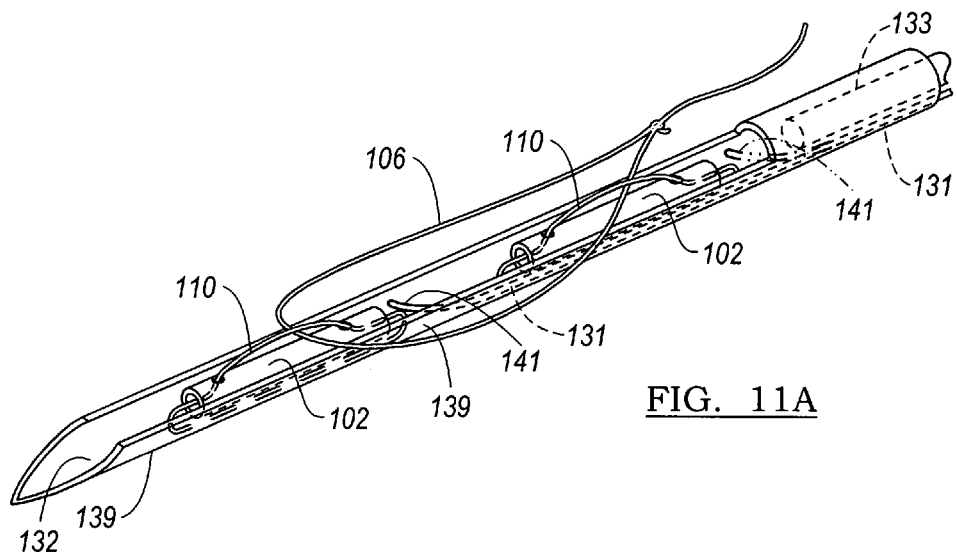
FIG. 11A is a side view of an inserter shown holding two soft-tissue repair assemblies according to the present teachings.
Figure 12:
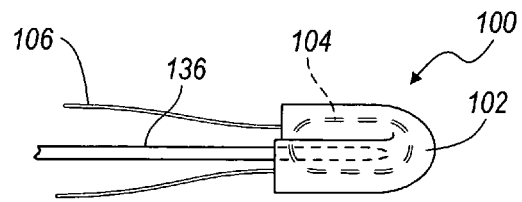
FIG. 12 is a side view of an inserter shown holding a soft-tissue repair assembly according to the present teachings.
Figure 13:
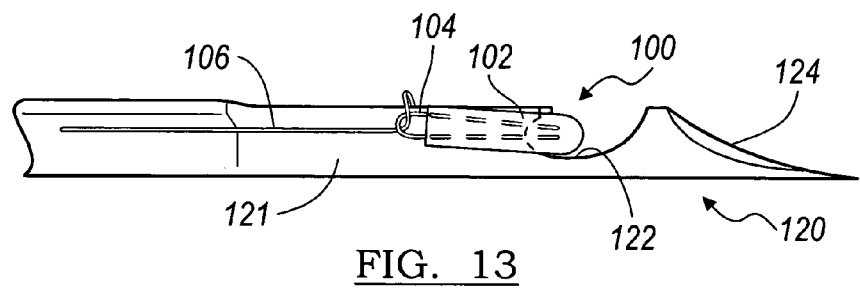
FIG. 13 is a side view of an inserter shown holding a soft-tissue repair assembly according to the present teachings.

Referring to FIGS. 10, 10A, 11 and 11A, one or more soft tissue assemblies 100 can be preloaded in a tubular inserter 130, such as the exemplary inserter 130 illustrated in FIG. 10A. The inserter 130 can include a handle 145 with a slider 137 and a shaft carrying a needle 139 having a bore 132. The flexible members 102 of the soft tissue assemblies 100 can be pushed out of the bore 132 using a plunger, a flexible pusher, such as a nitinol pusher, or other similar tool 131 operated by the slider 137. Referring to FIG. 11A, in an exemplary aspect two flexible members 102 are shown preloaded in the bore 132 of the needle 139 ahead of a stop 133. The flexible members 102 can be coupled by a strand 106 with a pre-knotted slip knot as discussed above, and can be separated by a curved end 141 of the flexible pusher 131. The curved end 141 of the flexible pusher 131 can push the first flexible member 102 out of the needle 139. The curved end 141 of the flexible pusher 131 can be straightened out as the flexible pusher 131 is retracted under the second flexible member 102, and positioned ahead of the stop 133 for pushing the second flexible member 102 out of the needle 139. Referring to FIG. 12, in another aspect, a single soft tissue assembly 100 can be loaded on a fork of a forked inserter 136.

In an exemplary soft tissue repair procedure, such as repair of a meniscal tear 82, one of the inserters 120, 130, 136, pre-loaded with at least one soft tissue repair assembly 100, can be inserted through a knee incision and through the meniscal tear 82. The flexible member 102 with the strand 106 coupled thereto can be implanted past the tear 82 on the posterior or outer surface 84 of the meniscal soft tissue 80, as illustrated, for example, in FIG. 4. The inserter 120, 130, 136 can then be removed leaving the strand ends 106a, 106b extending through the tear 82. Pulling the strand ends 106a, 106b away from the tear 82, causes the flexible member 102 to change shape into a suture securing shape, as discussed above, securely lodged on the outer surface soft tissue, without piercing, cutting or otherwise damaging tissue. The pulling action of the strand 106 reduces or closes the opening of the tear 82. Multiple soft-tissue repair assemblies 100 can be similarly implanted in daisy-chain fashion, as illustrated in FIG. 6, using the tubular inserter 130 with the multiple repair assemblies pre-loaded therein, or one by one, disconnectedly. Similar implanting procedures can be used for the soft-tissue repair assemblies 100 illustrated in FIGS. 7A, 7C, 7E, 7G, 7H, 7I and 7K. After implantation, the strand ends 106a, 106b or 110a, 110b can be secured with a knot, such as, for example, a pre-tied, self-locking slip knot, or other knot, and optionally with the help of a retainer, such as a retaining button, anchor, or other auxiliary retaining device (not shown).

During insertion and before implantation, the flexible member 102 can be supported and maintained in the bore 132 of the tubular inserter 130 in a linear shape, as illustrated in FIGS. 10, 11 and 11A. After deployment from the tubular inserter 130 for implantation relative to tissue, the flexible member 102 can change shape from a first shape into a second securing shape of curvilinear profile by tensioning the strand 106. In another aspect, the flexible member 102 can be supported or draped on the grooved inserter 120 or on the forked inserter 136 in a substantially folded or U-shape, as illustrated in FIGS. 14, 15 and 12. After deployment from the grooved inserter 120 or the forked inserter 136 for implantation relative to tissue, the flexible member 102 can be changed into a securing shape of curvilinear profile by tensioning the strand 106, as described above. It is noted that the substantially folded or U-shape, which is used with the grooved inserter 120 or the forked inserter 136 for loading the flexible member 102, is an intermediate shape between the first linear shape, and the securing shape of curvilinear profile that provides a bulky shape for securely lodging the flexible member 102 into tissue.

In another aspect, and referring to FIGS. 16-20, a soft-tissue repair assembly 100 can include one or more linear pipettes or pipette segments 150 over a strand 154 that can be used to reduce or close the tear 82. The repair-promoting pipette 150 can be made of resorbable or non-resorbable polymeric materials, collagen, allograft, such as segments of arteries or veins, or other solid-wall or woven/braided porous materials. The pipette 150 can also include perforations 162 for promoting additional biological flow. The strand 154 can pass through the tear 82 for reducing the opening of the tear 82, and can be secured with a knot 156. The soft-tissue repair assembly 100 can include one or more soft-tissue repair-promoting small tubes or pipettes 150, which can create conduits for vascularization and/or flow of nutrients, blood and other biological fluids and substances.

Figure 16:
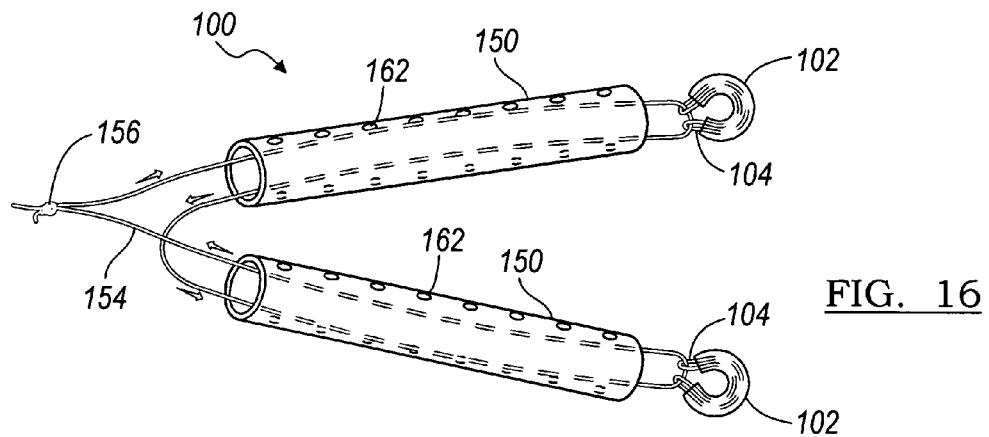
FIG. 16 is a perspective view of a soft-tissue repair assembly according to the present teachings.

Referring to FIG. 16, for example, the strand 154 can enter and pass through a first pipette 150 in one direction, pass through strand loop 104 of a first flexible member 102, pass through the first pipette 150 in the opposite direction and exit the first pipette 150, and similarly pass through the second pipette 150, the second flexible member 102, and out of the second pipette 150, as illustrated by the directional arrows along the strand 154.

Figure 17:
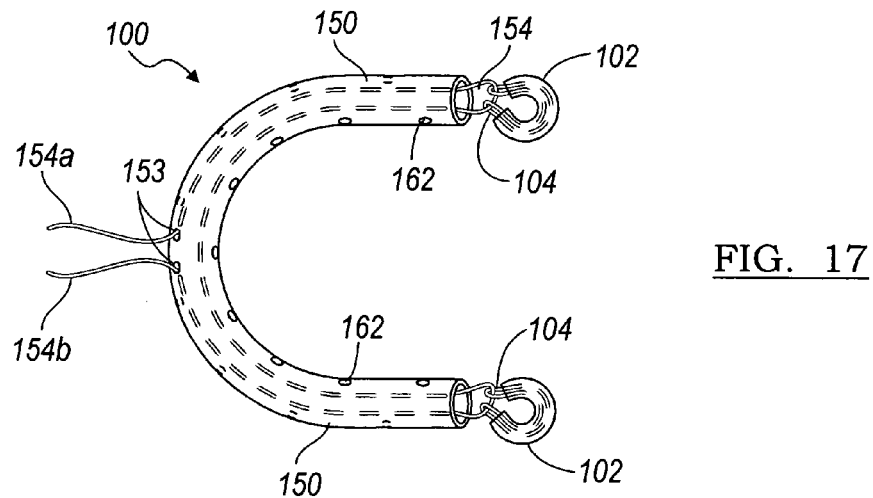
FIG. 17 is a perspective view of a soft-tissue repair assembly according to the present teachings.

Referring to FIG. 17, a single U-shaped pipette 150 can be used to run along the strand 154 between two flexible members 102. The strand ends 154a, 154b can exit the pipette 152 through small openings 153 at the bottom of the "U". The U-shape can be provided by using an originally straight, but flexible/compliant pipette 150 that changes shape while following the U-shaped portion of the strand 154 between the two flexible members 102, or by providing an originally curved pipette 150.

Figure 18:
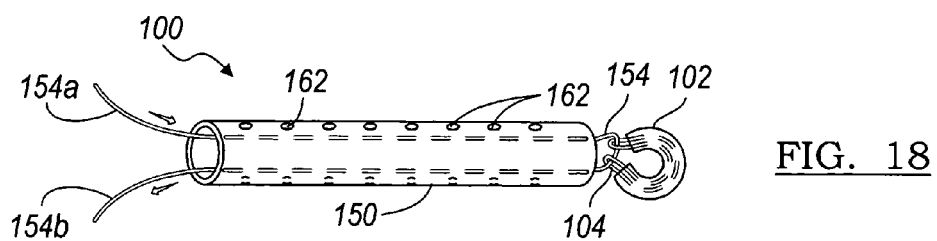
FIG. 18 is a perspective view of a soft-tissue repair assembly according to the present teachings.
Figure 19:
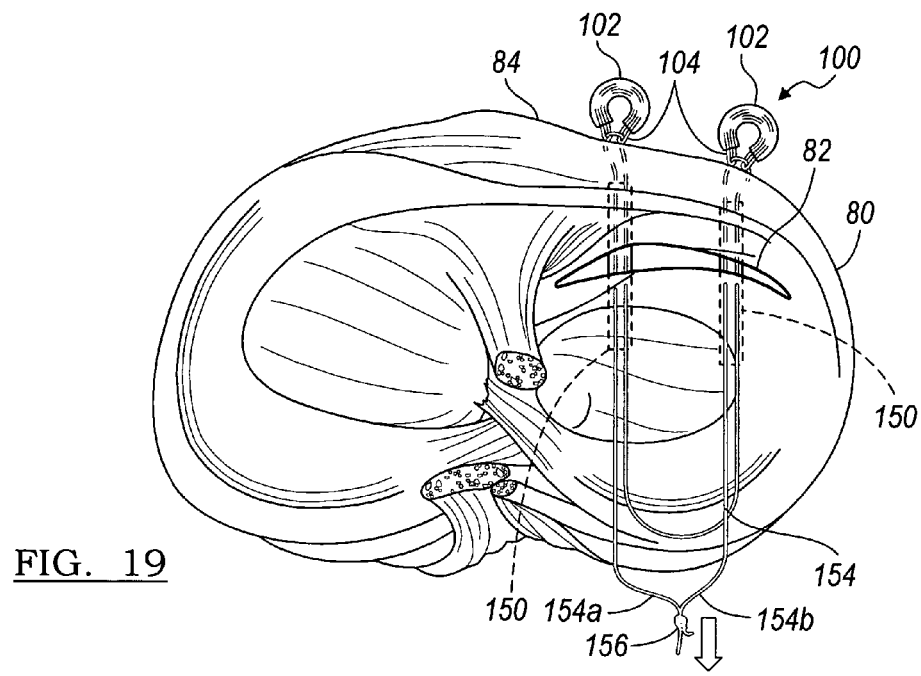
FIG. 19 is an environmental view of a soft-tissue repair assembly according to the present teachings.
Figure 20:
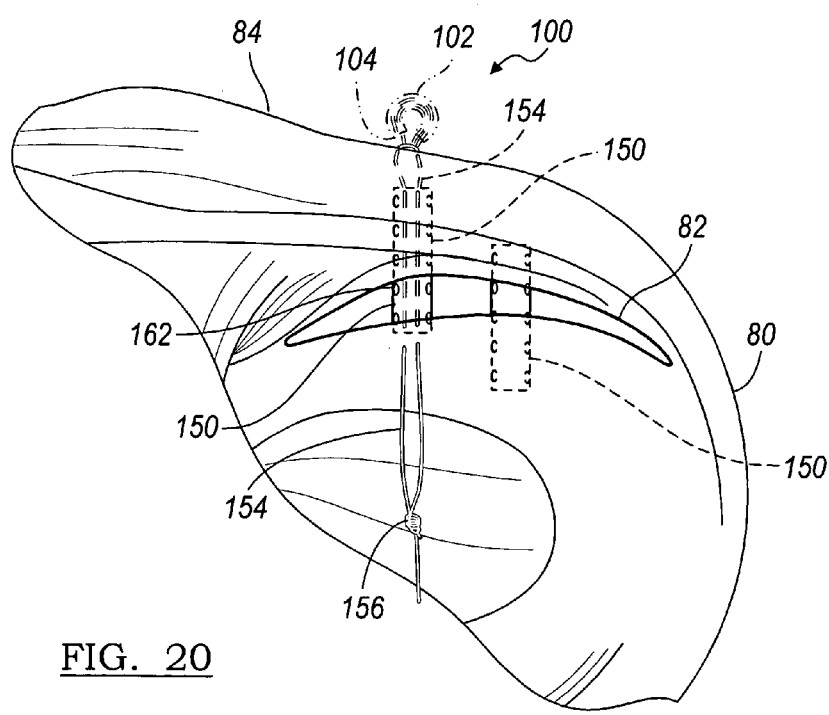
FIG. 20 is an environmental view of a soft-tissue repair assembly according to the present teachings.

Referring to FIGS. 18 and 20, a single pipette 150 can be used with one flexible member 102, with the strand 154 entering and exiting the pipette 150 in opposite directions before and after passing through the suture loop 104 of the flexible member 102. The flexible member 102 can be optionally used, or can be omitted entirely, as indicated by phantom lines in FIG. 20. Referring to FIG. 19, two pipettes 150 can be used over corresponding portions of the suture 154, with or without the use of flexible members 102. Additionally, one or more pipettes 150 can be used independently without any suture or strand 154 passing therethrough for promoting vascularization and healing.

Referring to FIGS. 4 and 6, the tissue repair assembly 100 can be used, for example, for implanting one flexible member 102, or multiple flexible members 102 for meniscal repair in an arthroscopic knee procedure. Referring to FIG. 4 an exemplary repair using a single flexible member 102 is illustrated. The flexible member 102 can be implanted using one of the inserters 120, 130, 136 discussed above and illustrated in FIGS. 8-15. The inserter 120, 130, 136 can inserted, with the flexible member 102 pre-loaded in a first shape, as discussed above, into meniscal tissue 80 through the meniscal tear 82. The flexible member 102 can be deployed from the inserter 120, 130, 136 by manual means or pushing the plunger 131 or other deploying device, and implanted on the posterior or outer surface 84 of the meniscal tissue 80 of the knee. The inserter 120, 130, 136 can be then withdrawn. At least one of ends 106a, 106b of the strand 106 can be pulled, causing the flexible member 102 to change to a second shape, as described above in connection with FIGS. 3, 4, 4A-7D. The thus-shaped flexible member 102 provides resistance against the outer meniscal surface 84, such that further tensioning the strand 106, causes the tear 82 to be reduced or closed. A slip knot, similar to the knot 156 illustrated in FIG. 20, and or another retaining device, such as a soft tissue anchor can be used to secure the strand 106 or the ends 106a, 106b to tissue.

Referring to FIGS. 6, 11, and 11A, the tubular inserter 130 can be used to implant multiple flexible members 102 on the posterior or other outer surface 84 of the meniscal tissue 80. The tubular inserter 130 can pre-loaded with multiple flexible members 102, which assume a first shape during loading and insertion, and which are coupled therebetween by the strand 106. After the first flexible member 102 is deployed from the inserter 130, as described above, in a first position on the outer surface 84, the inserter 130 can be withdrawn, re-inserted through the meniscal tear 82 and used to deploy a second flexible member 102 at a second position spaced apart from the first flexible member 102. After the last flexible member 102 is similarly deployed, the inserter 130 can be withdrawn, and the strand 106 tensioned by pulling one or both ends away from the tear 82, as illustrated in FIG. 6. Tensioning the strand 106 causes each of the flexible members 102 change to a second shape, thereby resisting further tensioning and causing the tear 82 to be reduced or closed.

The tubular inserter 130 can be similarly used to deploy one or more pipettes 150 independently, or with strands 154 and with or without one or more flexible members 102 for the configurations illustrated in FIGS. 16-20.

It will be appreciated that the soft-tissue repair assembly 100 of the present teachings provides an economically efficient, effective and versatile device for securing suture relative to soft tissue and repairing associated tears. Furthermore, the soft-tissue repair assembly 100 avoids or reduces tissue damage and relies on its rounded second shape for snug securing into tissue after implantation. Implantation can be facilitated by using an inserter according to the present teachings, and providing one or more flexible members 102 and connecting suture pre-loaded thereon. The new tissue repair techniques associated with the tissue repair assembly of the present teachings rely on existing surgeon skills and can be easily mastered.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A soft tissue repair assembly comprising:
an implantable integral deformable and flexible member defining an internal longitudinal bore and having first and second ends;
a first flexible strand passing through the flexible member, the first strand forming a closed loop, the closed loop passing at least partially through the longitudinal bore and having first and second loop ends extending outside the bore of the flexible member;
a second flexible strand separate from the first flexible strand, the second flexible strand coupled to the first and second loop ends of the first strand, the second strand extending substantially outside the flexible member, the second strand having first and second strand ends, such that pulling at least one of the first and second strand ends deforms the flexible member from a first shape suitable for insertion through soft tissue to a second shape suitable for securely lodging the soft tissue repair assembly relative to the soft tissue; and an inserter having a shaft extending along a longitudinal axis with a solid cross-section and a groove perpendicular to the longitudinal axis of the shaft, the groove formed on an outer surface of the shaft, the groove supporting the flexible member outside the shaft, such that the flexible member is folded in a U-shape over the groove with the second flexible strand coupled thereon.

2. The soft tissue repair assembly of claim 1, wherein the first and second loop ends of the first flexible strand extend through first and second wall openings defined through a wall of the flexible member.

3. The soft tissue repair assembly of claim 1, wherein the flexible member comprises braided material.

4. The soft tissue repair assembly of claim 1, wherein the flexible member comprises woven material.

5. The soft tissue repair assembly of claim 1, further comprising a protective sleeve over the flexible member.

6. The soft tissue repair assembly of claim 1, further comprising a separate elongated tubular conduit for vascularization, the conduit including an outer surface, a longitudinal inner bore and a plurality of perforations through the outer surface.

7. The soft tissue repair assembly of claim 6, wherein the second flexible strand passes through the tubular conduit.

8. The soft tissue assembly of claim 1, wherein relative to the soft tissue includes in soft tissue, adjacent the soft tissue or on an outer surface of the soft tissue.

9. A soft tissue repair assembly comprising:
an implantable integral deformable and flexible member in the form of a tube having first and second ends and defining an internal longitudinal bore between the first and second ends;
a first continuous flexible strand having first and second ends, the first and second ends forming respective first and second loop ends, the first strand passing once through the longitudinal bore forming a loop around the longitudinal bore, the first and second loop ends extending outside the bore of the tube through first and second openings away from the first and second ends of the tube; and
a second flexible strand separate from the first flexible strand, the second flexible strand coupled to the first and second loop ends of the first strand, the second strand extending substantially outside the tube, the second strand having first and second strand ends, such that pulling at least one of the first and second strand ends deforms the tube from a first shape suitable for insertion through soft tissue to a second shape suitable for securely lodging the soft tissue repair assembly relative to the soft tissue, wherein the first shape is circular and the second shape is an eight-like shape; and an inserter wherein the inserter includes a shaft with a solid cross-section and a longitudinal axis, the shaft defining a groove on an outer surface of the shaft, the groove being perpendicular to the longitudinal axis of the shaft, wherein the flexible member is supported on the groove outside the shaft.

10. The soft tissue repair assembly of claim 9, wherein the flexible member comprises woven material.

11. The soft tissue repair assembly of claim 9, wherein the flexible member comprises braided material.

12. The soft tissue repair assembly of claim 9, further comprising a separate elongated tubular conduit for vascularization preloaded on the inserter, the conduit including an outer surface, a longitudinal inner bore and a plurality of perforations through the outer surface.

13. A soft tissue repair assembly comprising:
an implantable integral deformable and flexible member forming a tube having first and second ends and defining an internal longitudinal bore between the first and second ends;
a continuous flexible strand having first and second strand ends, the strand passing once through longitudinal bore such that the first strand end exits the first end of the tube and passes through a first hole of the tube through the tube and the second strand end exits the second end of the tube and passes through a second hole of the tube through the tube, the first and second holes intermediate the first and second ends of the tube, such that pulling the first and second strand ends deforms the tube from a first shape suitable for insertion through soft tissue to a second shape suitable for securely lodging the soft tissue repair assembly relative to the soft tissue, wherein first shape is substantially linear and the deformed second shape is a pretzel-like shape including curved portions; and an inserter including a shaft having a needle, the needle defining a longitudinal bore into which the tubular member is preloaded, the inserter including a flexible and retractable pusher, wherein the pusher includes a curved end that is straightened when the pusher is retracted under one of the tubular members the pusher operable to push the tubular members out of the needle.

14. A soft tissue repair assembly comprising:
a first inserter, the first inserter including a shaft with a solid cross-section and a longitudinal axis, the shaft defining a groove on an outer surface of the shaft, the groove perpendicular to the longitudinal axis of the shaft;
a first integral deformable and flexible tubular member, the first tubular member preloaded on the first inserter in a first shape, wherein the first shape is a substantially folded U-shape, the first tubular member supported on the groove outside the shaft, the first tubular member comprising woven fabric and having first and second open ends defining an internal longitudinal bore extending between the first and second ends of the first tubular member;
a first flexible strand forming a continuous loop, the continuous loop inserted within the longitudinal bore of the first tubular member such that first and second loop ends extend through the first and second ends of the first tubular member; and
a second flexible strand separate from the first flexible strand, the second flexible strand passing through the first and second loop ends of the first flexible strand, the second flexible strand operable by pulling to deform the shape of the first tubular member from the first shape to a second shape after implantation, the second shape being a U-shape bulkier than the first shape and suitable for securely lodging the first tubular member relative to soft tissue.

15. The soft tissue repair assembly of claim 14, further comprising:
a second integral deformable and flexible tubular member, the second tubular member deformable from a first shape for insertion through tissue to a second shape after implantation, the second tubular member comprising woven fabric and having first and second open ends defining an internal longitudinal bore extending between the first and second ends of the second tubular member;
a third flexible strand forming a continuous loop, the continuous loop inserted within the longitudinal bore of the second tubular member such that first and second loop ends of the third flexible strand extend through the first and second ends of the second tubular member; and wherein the second flexible strand passes through the first and second loop ends of the second flexible strand for deforming both the first and second tubular members.

16. The soft tissue repair assembly of claim 14, further comprising a second inserter.

17. A soft tissue repair assembly comprising:

a plurality of integral deformable and flexible tubular members, each tubular member formed of woven fabric and having first and second open ends defining a corresponding internal longitudinal bore extending between the first and second ends of each tubular member;

a plurality of flexible strands, each flexible strand forming a separate continuous loop, each continuous loop inserted within the longitudinal bore of a corresponding tubular member such that first and second loop ends extend through the first and second ends of the corresponding tubular member;

an additional flexible strand member separate from the plurality of flexible strands, the additional flexible strand member passing through the first and second loop ends of the each flexible strand, the additional flexible strand member operable by pulling to deform the shape of each tubular member from a first shape to a second shape after implantation, wherein the second shape is a bulkier shape than the first shape and suitable for securely lodging the flexible member relative to soft tissue; and an inserter including a shaft having a needle, the needle defining a longitudinal bore into which the plurality tubular members are preloaded, the inserter including a flexible and retractable pusher, wherein the pusher includes a curved end that is straightened when the pusher is retracted under one of the tubular members, the pusher operable to push each of the tubular members out of the needle sequentially.

* * * * *

UNITED STATES PATENT AND TRADEMARK OFFICE
CERTIFICATE OF CORRECTION

PATENT NO. : 7,749,250 B2
APPLICATION NO. : 11/347661
DATED : July 6, 2010
INVENTOR(S) : Kevin T. Stone et al.

It is certified that error appears in the above-identified patent and that said Letters Patent is hereby corrected as shown below:

Column 3
Line 29, "include" should be --including--.

Column 3
Line 55, "cofton" should be --cotton--.

Column 4
Line 47, insert --that-- between "such" and "the".

Column 5
Line 10, "snuggly" should be --snugly--.

Column 5
Line 14, insert --with-- between "associated" and "sharp-element".

Column 5
Line 39, "flexile" should be --flexible--.

Column 7
Line 55, insert --be-- between "can" and "inserted".

Column 8
Line 8, insert --be-- between "can" and "pre-loaded".

Column 8
Line 20, insert --to-- between "102" and "change".

Column 9
Line 40, delete "and".

Signed and Sealed this

Twelfth Day of October, 2010

David J. Kappos
*Director of the United States Patent and Trademark Office*